United States Patent
Liu (10) Patent No.: US 9,759,818 B2
(45) Date of Patent: Sep. 12, 2017

(54) DIGITAL FLAT PANEL DETECTOR WITH SQUIRCLE SHAPE

(71) Applicant: General Electric Company, Schenectady, NY (US)

(72) Inventor: James Zhengshe Liu, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 348 days.

(21) Appl. No.: 14/478,655

(22) Filed: Sep. 5, 2014

(65) Prior Publication Data

US 2016/0070004 A1 Mar. 10, 2016

(51) Int. Cl.
*G01T 1/20* (2006.01)
*G01T 1/24* (2006.01)
*H01L 27/146* (2006.01)
*A61B 6/00* (2006.01)

(52) U.S. Cl.
CPC ............ *G01T 1/20* (2013.01); *G01T 1/24* (2013.01); *H01L 27/14607* (2013.01); *A61B 6/4233* (2013.01)

(58) Field of Classification Search
CPC ....... A61B 6/42; A61B 6/4208; A61B 6/4233; A61B 6/4283; A61B 6/44; G01T 1/24; G01T 1/244; H01L 27/14601; H01L 27/14607
See application file for complete search history.

(56) References Cited

U.S. PATENT DOCUMENTS

| | | | | |
|---|---|---|---|---|
| 5,291,010 A | * | 3/1994 | Tsuji | A61B 1/05 250/208.1 |
| 5,510,623 A | * | 4/1996 | Sayag | G01T 1/2928 250/208.1 |
| 6,527,442 B2 | * | 3/2003 | Carroll | A61B 6/14 348/E3.02 |
| 6,794,654 B1 | * | 9/2004 | Hansen | H01L 27/14658 250/366 |
| 7,281,847 B2 | * | 10/2007 | Kokkaliaris | A61B 6/145 348/E5.026 |
| 7,462,807 B2 | * | 12/2008 | Caupain | H01L 27/1463 250/208.1 |

(Continued)

OTHER PUBLICATIONS

International Search Report for International Application No. PCT/US2015/048146, mail date Dec. 14, 2015, 3 pages.

*Primary Examiner* — Thomas R Artman (57) ABSTRACT

Systems and methods for generating an X-ray image using a digital flat panel detector with a squircle shape are described. The flat panel X-ray detector contains a circuit board, a light imager electrically connected to the circuit board, and a scintillator coupled on the light imager. The detector has superellipse shape or a cornerless shape with a first substantially straight edge and a second substantially straight edge running substantially perpendicular to the first edge, wherein the first and second edges do not physically intersect with each other at 90 degrees. The flat panel detector with this shape can be used in an x-ray imaging system that uses the detector to detect x-rays and produce an x-ray image. With this shape, the active sensing area of the detector can be similar to those currently available with rectangular or square flat panel detectors, while using less material to create the detector.

14 Claims, 9 Drawing Sheets

(56) References Cited

U.S. PATENT DOCUMENTS

| | | | |
|---|---|---|---|
| 8,366,318 B2* | 2/2013 | Zeller | A61B 6/145 |
| | | | 378/168 |
| 8,942,346 B2* | 1/2015 | Nicholson | A61B 6/06 |
| | | | 378/147 |
| 9,259,197 B2* | 2/2016 | Zeller | A61B 6/145 |
| 9,385,149 B2* | 7/2016 | Rohr | H01L 27/14603 |
| 2002/0080265 A1 | 6/2002 | Hoffman | |
| 2006/0126797 A1* | 6/2006 | Hoernig | A61B 6/504 |
| | | | 378/207 |
| 2008/0078940 A1 | 4/2008 | Castleberry et al. | |
| 2008/0128698 A1* | 6/2008 | Martin | G03F 7/70433 |
| | | | 257/55 |
| 2012/0267535 A1 | 10/2012 | Nakatsugawa et al. | |
| 2013/0170616 A1 | 7/2013 | Mruthyunjaya et al. | |
| 2013/0256543 A1* | 10/2013 | Granfors | G01T 1/2018 |
| | | | 250/370.09 |
| 2013/0259195 A1* | 10/2013 | Nicholson | A61B 6/06 |
| | | | 378/62 |
| 2015/0303228 A1* | 10/2015 | Rohr | H01L 27/14603 |
| | | | 250/366 |
| 2016/0070004 A1* | 3/2016 | Liu | G01T 1/20 |
| | | | 378/62 |

* cited by examiner

DIGITAL FLAT PANEL DETECTOR WITH SQUIRCLE SHAPE

FIELD

This application relates generally to systems and methods for obtaining and displaying an X-ray image. In particular, this application relates to systems and methods for generating an X-ray image using a digital flat panel detector with a squircle shape.

BACKGROUND

A typical X-ray imaging system comprises an X-ray source and an X-ray detector. The X-rays that are emitted from the X-ray source can impinge on the X-ray detector and provide an X-ray image of the object (or objects) that are placed between the X-ray source and the X-ray detector. In one type of X-ray imaging system, a fluoroscopic imaging system, the X-ray detector is often an image intensifier or, more recently, a flat panel digital detector. The flat panel detector contains a layer of scintillator material which converts the x-rays into light. Behind the scintillator layer is a detector array containing multiple pixels arranged in a grid. Each pixel contains a photodiode that generates an electrical signal proportional to the light from the scintillator layer in front of the pixel. The signals from the photodiodes are amplified by electronics to produce a digital representation of the x-ray image of the object that is located between the X-ray source and the X-ray detector.

SUMMARY

This application relates to systems and methods for generating an X-ray image using a digital flat panel detector with a squircle shape. The flat panel X-ray detector contains a circuit board, a light imager such as a CMOS wafer electrically connected to the circuit board, and a scintillator on the light imager. The detector has a superellipse shape or a cornerless shape with a first substantially straight edge and a second substantially straight edge running substantially perpendicular to the first edge, wherein the first and second edges do not physically intersect with each other at 90 degrees. The flat panel detector with such a shape can be used in an x-ray imaging system that uses the detector to detect x-rays and produce an x-ray image. With this shape, the active sensing area of the detector can be similar to those currently available with rectangular or square flat panel detectors, while using less material to create the detector.

BRIEF DESCRIPTION OF THE DRAWINGS

The following description can be better understood in light of the Figures, in which.

The Figures illustrate specific aspects of the systems and methods for generating an X-ray image using a digital flat panel detector with a squircle shape. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices. Moreover, for clarity, the Figures may show simplified or partial views, and the dimensions of elements in the Figures may be exaggerated or otherwise not in proportion.

DETAILED DESCRIPTION

The following description supplies specific details in order to provide a thorough understanding. Nevertheless, the skilled artisan would understand that the described systems and methods for obtaining and displaying collimated X-ray images can be implemented and used without employing these specific details. Indeed, the described systems and methods can be placed into practice by modifying the illustrated devices and methods and can be used in conjunction with any other apparatus and techniques conventionally used in the industry. For example, while the description below focuses on systems and methods for displaying X-ray images that were created using a fluoroscopic X-ray device that obtains X-ray images in near real time, the described systems and methods (or portions thereof) can be used with any other suitable device or technique. For instance, the described systems and methods (or portions thereof) may be used with X-ray devices that produce traditional, plain X-ray images.

As the terms on, attached to, connected to, or coupled to are used herein, one object (e.g., a material, an element, a structure, etc.) can be on, attached to, connected to, or coupled to another object, regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, horizontal, vertical, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Further, the terms a, an, and one may each be interchangeable with the terms at least one and one or more. Additionally, the terms X-ray image, image, collimated image, and collimated X-ray image may refer to an X-ray image that is produced from a portion of an X-ray detector that is exposed to an X-ray beam that has been collimated with a collimator.

In some embodiments, the term square may refer to a shape with four sides of equal length that also has four 90 degree corners. The term circle, in some embodiments, may refer to a closed plane curve having all points at a given distance from a common center point. The term squircle, in some embodiments, may refer to a Boolean intersection of a concentric circle and square, where the final shape has an area less than either the circle or the square. The term squircle, in other embodiments, may refer to a Boolean intersection of a square and a concentric circle whose diameter is greater than the length of the side of the square, but less than the diagonal of the square. The term mathematical squircle, in some embodiments, may refer to a specific type of superellipse with a shape between those of a concentric square and circle and may be expressed as a quadric planar curve or as a quadric Cartesian equation. A mathematical squircle, as opposed to the squircle shapes immediately above, maintains the tangent continuity between the circular corners with the flatter edges of a superellipse. The terms rounded square and rounded rectangle, in some embodiments, may respectively refer to a square or a rectangle with fillets breaking the corners (e.g., circular corners that are tangent to the edges of the square or rectangle). Additionally, in some embodiments the terms chamfered square and chamfered rectangle may respectively refer to a square and rectangle having any number of chamfers breaking their corners.

Figure 1:
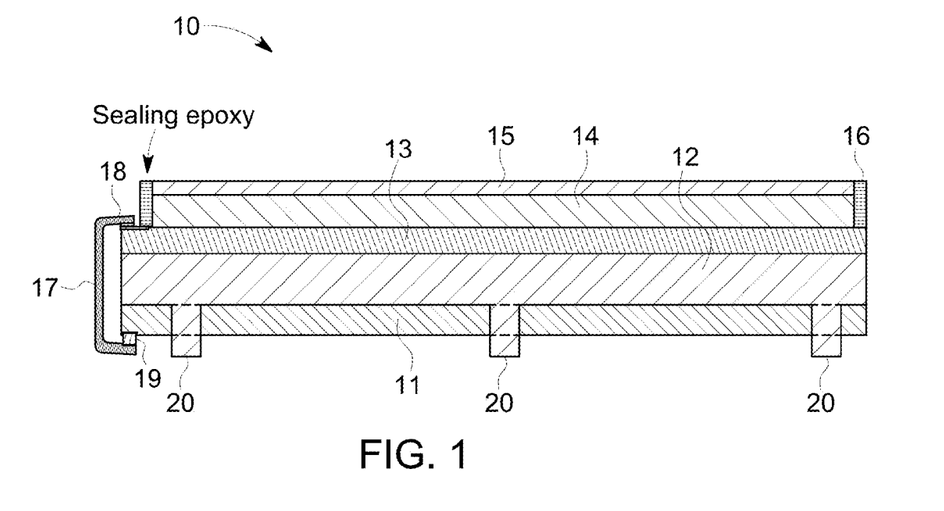
FIG. 1 shows a side view of some embodiments of a squircle-shaped flat panel detector.

Some embodiments of a squircle-shaped (SS) flat panel detector are shown in FIG. 1. In FIG. 1, the flat panel detector (or detector assembly) 10 contains a circuit board 11, a supporting substrate 12, a light imager 13, scintillator 14, scintillator cover 15, sealant 16, and connector 17. In FIG. 1, the detector controlling electronics are structured underneath the supporting substrate and connected to the light imager 13 through the connector 17 in order to maintain a minimal x-y dimension. The supporting substrate is connected to the detector cover (not shown) with the connection poles 20 through suspensive components (not shown). The components of the detector 10 illustrated in FIG. 1 may represent only some of the components present in such detection systems. For example, these detectors 10 may include other electronics, battery and wireless transceiver, communication and power supply cables, an outer cover or sleeve, suspensive components, etc.

The detector 10 also contains a supporting substrate 12. This substrate 12 can be used primarily to provide support to the remainder of components in the detector 10. Accordingly, the substrate 12 can be made of any material and/or structure that provides this support. In some configurations, the substrate 12 can be made from metal, metal alloy, plastic, a composite material, carbon fiber, or a combination of these materials.

FIG. 1 illustrates some embodiments of the detector 10 (e.g., a CMOS based detector) that include a scintillator layer (or scintillator 14) that is disposed on a light imager 13 (e.g., CMOS light imager). The scintillator 14 may be fabricated from any scintillator compositions such as Cesium Iodide (CsI) or Lutetium oxide (Lu2O3).

In some configurations, the light imager 13 may include a photodetection layer. Some conventional detached scintillator plates (e.g., in CMOS based detectors) are coated by a protective film that exhibits poor light reflection and transparency properties which results in sub-optimal performance of the photodetection capabilities of the X-ray detector. To alleviate this deficiency, the scintillator 14 in detector 10 can be directly disposed upon the photodetection layer of the light imager 13. Thus, in these configurations, the scintillator 14 can directly contact the photodetection layer.

The scintillator 14 and the photodetection layer of the light imager 13 functions in combination to convert X-ray photons to electrical signals for acquiring and processing image data. Generally, X-ray photons are emitted from a radiation source (such as an x-ray source), traverse the area in which an object or subject is positioned, and then collide with the scintillator 14. The scintillator 14 converts the X-ray photons to lower energy optical photons and is designed to emit light proportional to the energy and the amount of X-rays absorbed. As such, light emissions will be higher in those regions of the scintillator 14 where more X-rays were received. Since the composition of the object or subject will attenuate the X-rays projected by the radiation source to varying degrees, the energy level and the amount of the X-ray photons colliding with the scintillator 14 will not be uniform across the scintillator 14. The non-uniform collision results in the variation of light emission that will be used to generate contrast in the reconstructed image.

After the X-ray photons are converted to optical photons, the resulting optical photons emitted by the scintillator 14 are detected by the photodetection layer of the light imager 13. The photodetection layer may contain an array of photosensitive elements or detector elements that store an electrical charge in proportion to the quantity of incident light absorbed by the respective detector elements. Generally, each detector element has a light sensitive region and an electronically-controlled region for the storage and output of electrical charge from that detector element. The light sensitive region may be composed of a photodiode, which absorbs light and subsequently creates electronic charges stored in the photodiode or a storage capacitor. After exposure, the electrical charge in each detector element is read out via logic-controlled electronics and processed by the imaging system.

In some alternative embodiments, the light imager 13 may be a charged coupled device (CCD) imager, amorphous silicon receptor light imager, or suitable field-effect transistor controlled light imager. The scintillator 14 may be deposited directly onto and in direct contact with any light imager 13 to prevent the reduction in useful light photons as discussed above.

To protect the scintillator 14 from moisture and to provide structural support, a scintillator cover (or cover) 15 may be placed over the surface of the scintillator 14, as shown in FIG. 1. The cover 15 may be fabricated with metal, metal alloy, plastic, a composite material, or a combination of the above material. In some embodiments, the cover 15 may be composed of low x-ray attenuation, lightweight, durable composite material such as a carbon fiber.

In some embodiments, the detector 10 may include a moisture blocking layer or sealant to block moisture from entering into the scintillator material. Thus, as illustrated in FIG. 1, the detector 10 includes a sealant 16 that can be disposed around the side surface of the cover 15 as well as the outer edges of the scintillator 14.

The detector 10 also contains an electrical connection between the light imager 13 and the circuit board 11. In the embodiments illustrated in FIG. 1, this electrical connection comprises flex connector 17. The flex connector is used to connect the circuit board 11 and the light imager 13 (both of which are substantially rigid) with room for the movement of one or both. The light imager 13 in FIG. 1 may shift due to mechanical force such as vibration, yet the flex connector 17 maintains the electrical connection despite this movement. The flex connector 17 can be connected to the light imager 13 and the circuit board 11 using any connection, including a thermosonic bond 18 to the light imager 13 and Hirose-type connector 19 to the circuit board 11.

Figure 2:
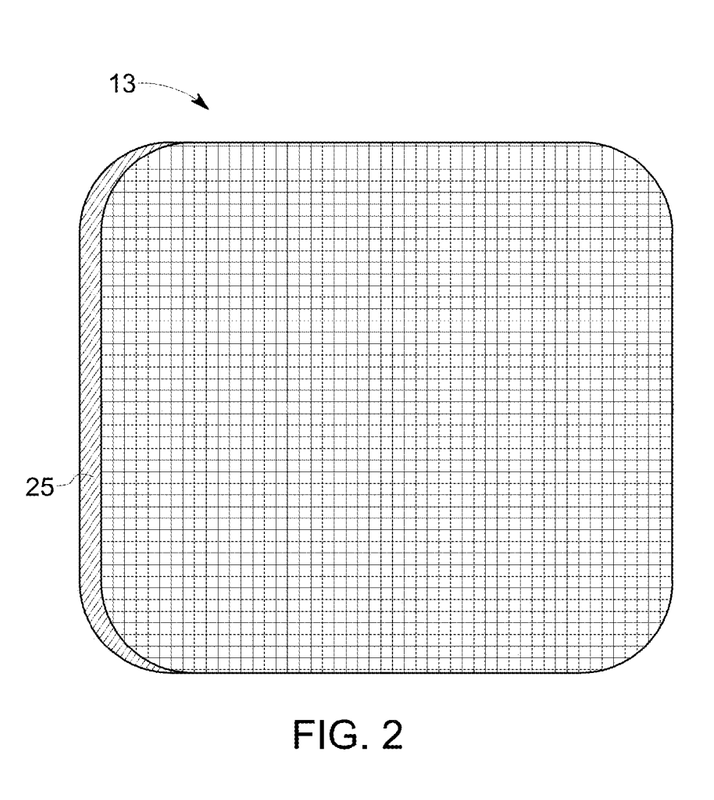
FIG. 2 shows a top view of some embodiments of the light imager of a squircle-shaped flat panel detector.

An exemplary top view of some embodiments of the detector assembly 10 is illustrated in FIG. 2. In FIG. 2, the contacting finger area 25 of the light imager 13 is connected to the flex connector 17. The contacting finger area 25 can include the column A/D convertors, the scanning driving circuitry, and the contacting pads, that are connected to the detector controlling electronics using the flex connector 17.

The detector 10 may be assembled by any method which forms the structure illustrated in FIG. 1. In some embodiments, the scintillator 14 can be deposited onto a photodetection layer of a light imager 13. The method may also include depositing a light reflector onto the top surface of the scintillator 14. The resulting structure is then provided on the supporting substrate 12 that has already been connected to the circuit board 11. The cover 15, such as a carbon fiber cover, may be deposited onto the light reflector. The sealant 16 can then be provided on the side surfaces of the scintillator 14 and the cover 15. Finally, the flex connector 17 is then bonded to the upper surface of the light imager 13 and the bottom surface of the circuit board 11, resulting in the detector assembly as depicted in FIG. 1.

In other embodiments, the electrical connection between the CMOS light imager 13 and the circuit board 11 can be configured differently. In these embodiments, the column A/D convertors as well as the scanning driving circuitries are built inside the pixel array and the contacting trace on the back of the panel can be accomplished using Through-Silicon-Via (TSV) technology. Compared to the embodiments depicted in FIG. 1, this configuration would yield a smaller x-y dimension of the detector assembly.

Figure 3:
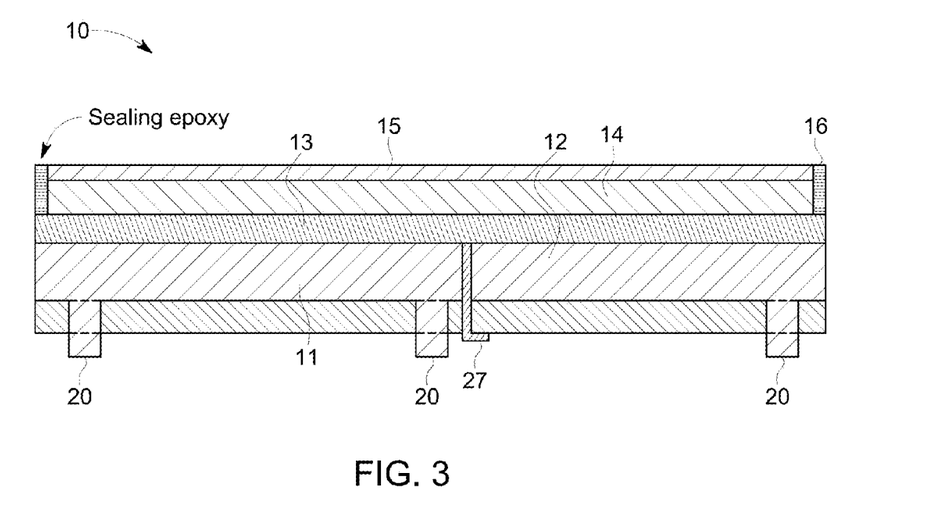
FIG. 3 shows a side view of other embodiments of a squircle-shaped flat panel detector.

Some of these embodiments are depicted in FIG. 3. The components of this detector assembly are substantially similar to those depicted in FIG. 1, except that the flex connector 17 has been configured as flex connector 27 which is configured to re-route the electrical signals from the CMOS light imager 13 through the supporting substrate 12 and then to the circuit board 11. In some embodiments, the light imager 13 may be glued onto the substrate 12 and the sealant 16 may be applied between the scintillator cover 15 and the substrate 12.

Figure 4:
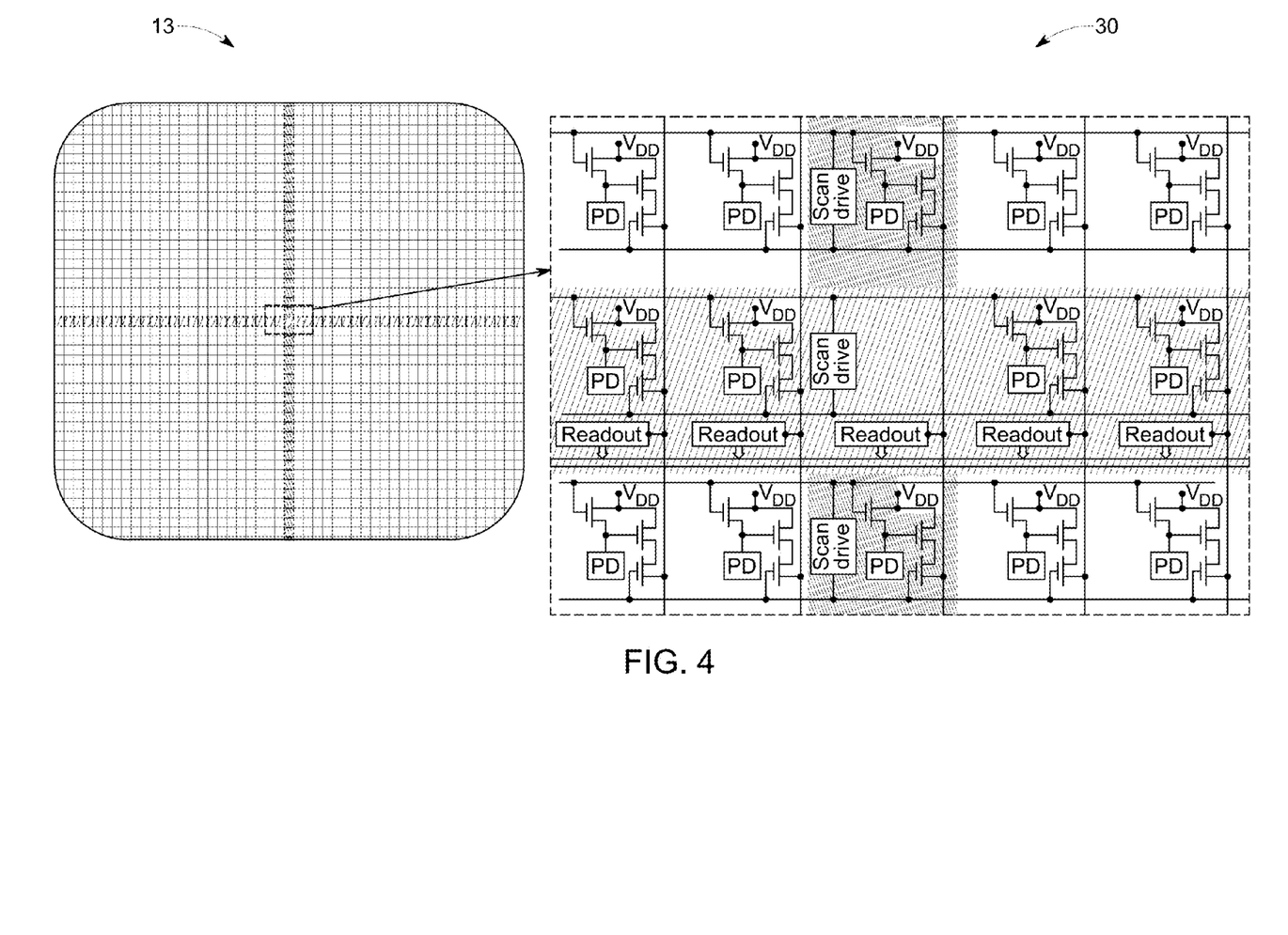
FIG. 4 shows a top view of other embodiments of the light imager of a squircle-shaped flat panel detector.

FIG. 4 depicts schematically the two-dimensional (2D) array of the pixels as well as the scanning driver circuitry and the readout circuitry that can be used in some configurations of the detector assembly 10. In FIG. 4, the scan driver circuitries 30 share the real estate space with the pixels located on one column of the array and the readout circuitries share the space with the pixels on one row of the array. The readout row and the scanning column are located away from the rounded corner of the squircle to ensure that all pixels in the 2D array are accessible. The scanning circuitries sequentially select a row of pixels to read and then reset those pixels after reading. The readout circuitries sample the analog pixel signal, digitize the analog signal, and transfer the digitized pixel values one by one to the detector controlling board via a data bus. The introducing of the A/D in the readout circuitries and the use of data bus greatly reduces the number of wires to transfer the pixel data, which reduces the number of contacting finger and simplifies the TSV technology that is used.

FIGS. 5-12 show some embodiments of the shapes of the SS flat panel detector. In some configurations, the shape can be a superellipse shape or a cornerless shape. A cornerless shape comprises a shape missing one or more 90 degree corners (i.e., two edges that run substantially perpendicular to each other without containing a 90 degree corner between those edges). The cornerless shape may contain corners with a degree less than 90 degrees. Some examples of such shapes include a rounded square, a rounded rectangle, a chamfered square, a chamfered rectangular, a rectangle with curved borders, a truncated circle, an octagon, a hexagon, or any other suitable shape.

Where the detector has the shape of a superellipse, it can have any suitable characteristic that allows it to be classified as a superellipse (as described herein). By way of example, the aperture can be a shape that is generated by a formula selected from: (i) $|x-a|^n+|y-b|^n=|r|^n$, and (ii)

$$\left|\frac{(x-a)}{r_a}\right|^n + \left|\frac{(y-b)}{r_b}\right|^n = 1,$$

wherein a, b is the center point; r is the minor; n is equal to 4; and $r_a$ and $r_b$ are the semi-major and semi-minor axes, respectively.

Figure 5:
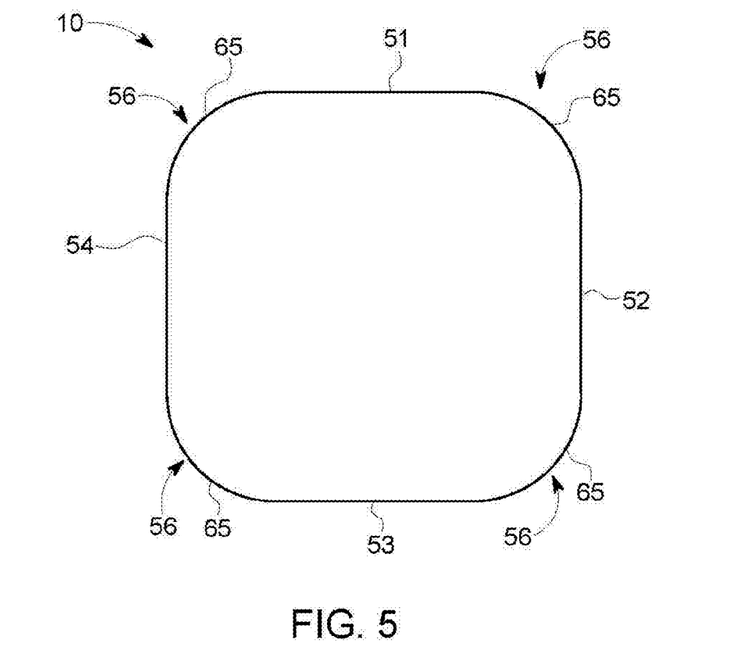
FIGS. 5-12 depict some examples of the shape of a squircle-shaped flat panel detector.

FIG. 5 depicts some embodiments of the shape of a superellipse. In FIG. 5, the detector contains a first 51 and second 52 images edge, a second 52 and third 53 edge, a third 53 and fourth 54 edge, and a fourth 54 and first 51 edge, respectively, which do not physically intersect at a 90 degree corner. Rather, the detector corners 56 are removed so the detector's first edge 51 and third edge 53 are each separated from the second edge 52 and fourth edge 54 by a non-linear (i.e., substantially curved) image border.

Figure 6:
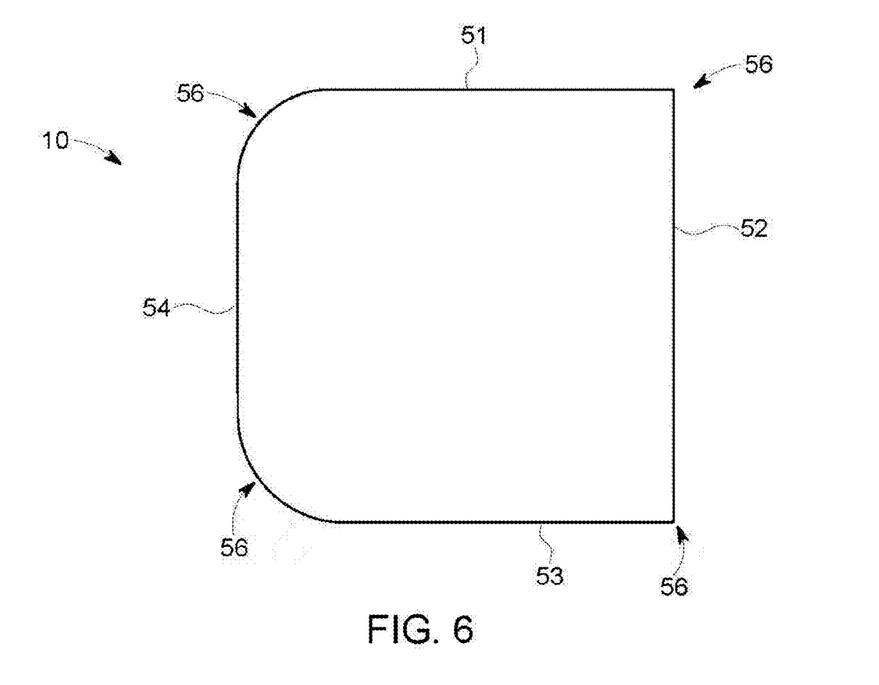

FIG. 6 shows other embodiments of shape of the flat panel detector. In FIG. 6, the detector contains two corners 56 that lack a 90 degree corner between two perpendicular edges (e.g., between the third 53 and fourth 54 edges and between the first 51 and fourth 54 edges). The configuration in FIG. 6 can be useful for mammographic applications. In this configuration, the edge with the two right corners can be placed against the chest wall of a patient. So there will be no patient anatomy on the two corners of the opposite side, allowing them to be rounded.

Figure 7:
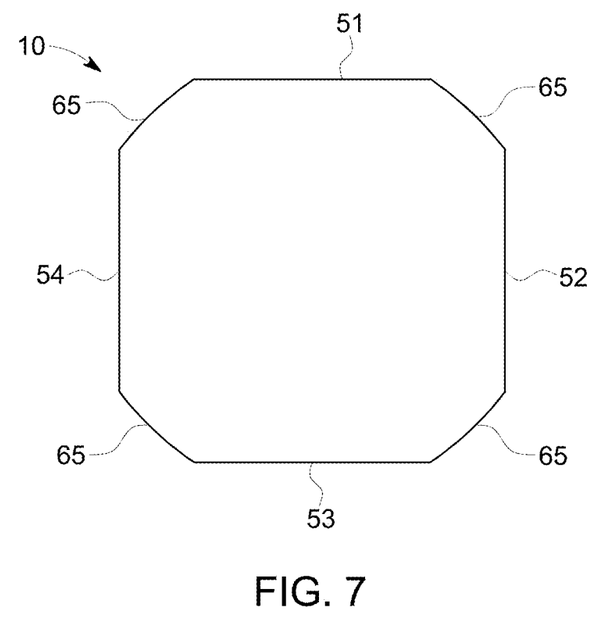
Figure 8:
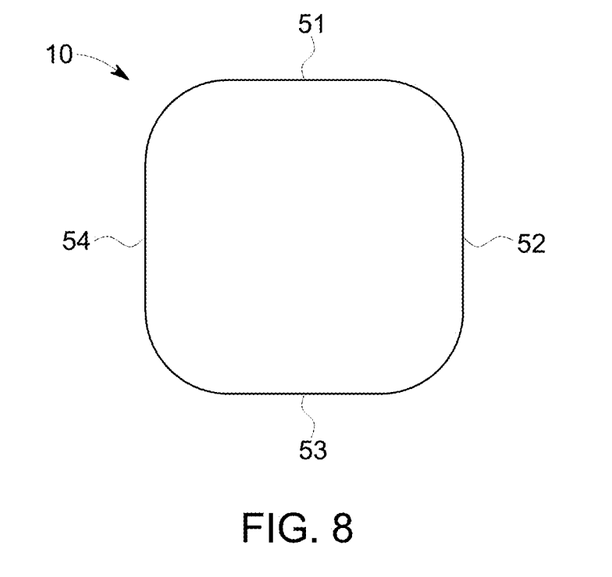
Figure 9:
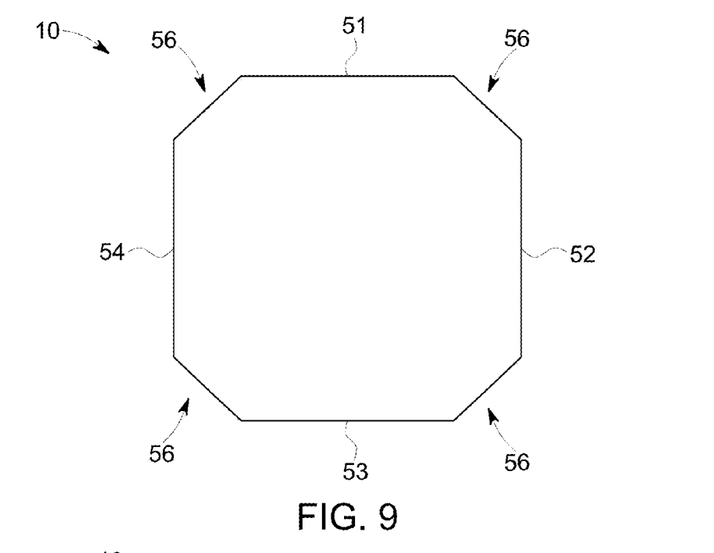

Indeed, the detector can have any suitably shaped border between adjacent edges that run perpendicular to each other. Some examples of suitable borders include a border with the shape of an arc of a circle, a chamfered border, a rounded border, a convex border, a concave border, a zigzag border, a curved border, an irregular border, etc. In this regard, FIG. 7 shows some embodiments in which all four borders comprise an arc-shaped border 65. FIG. 8 shows some configurations in which the each of the detector's four borders comprises a rounded border so that the detector comprises a rounded square (or rounded rectangle in other configurations). And FIG. 9 shows some embodiments in which each of the detector's four borders 63 comprises a chamfered border so that the detector comprises a chamfered square (or chamfered rectangle in other configurations).

Figure 10:
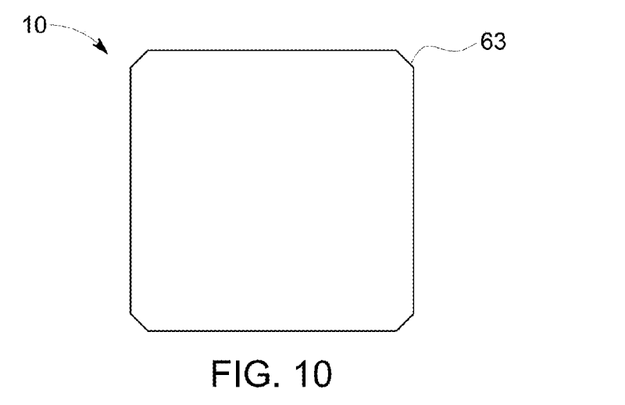
Figure 11:
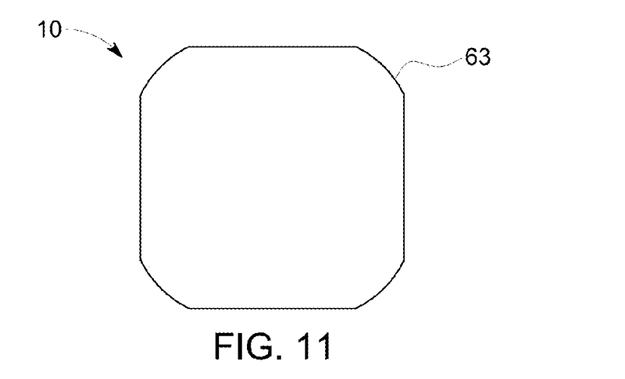
Figure 12:
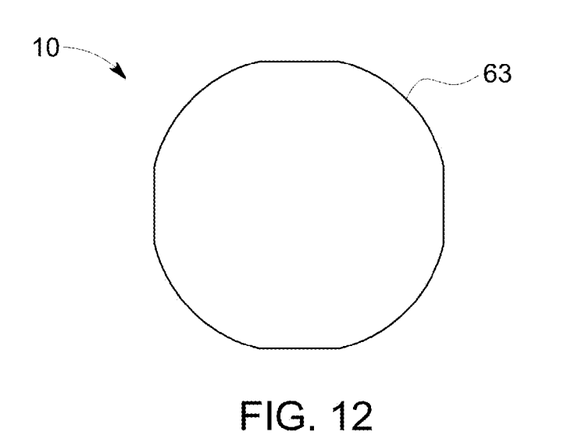

In some configurations a border separates two substantially perpendicular edges. In these configurations, the borders can have any suitable shape that allows the detector to function as described herein. By way of example, FIG. 10 shows the detector 10 having predominantly square shaped, FIG. 12 shows a detector that is predominantly circular in shape, and FIG. 11 the detector 10 has a shape between those shown in FIGS. 10 and 12.

Figure 13:
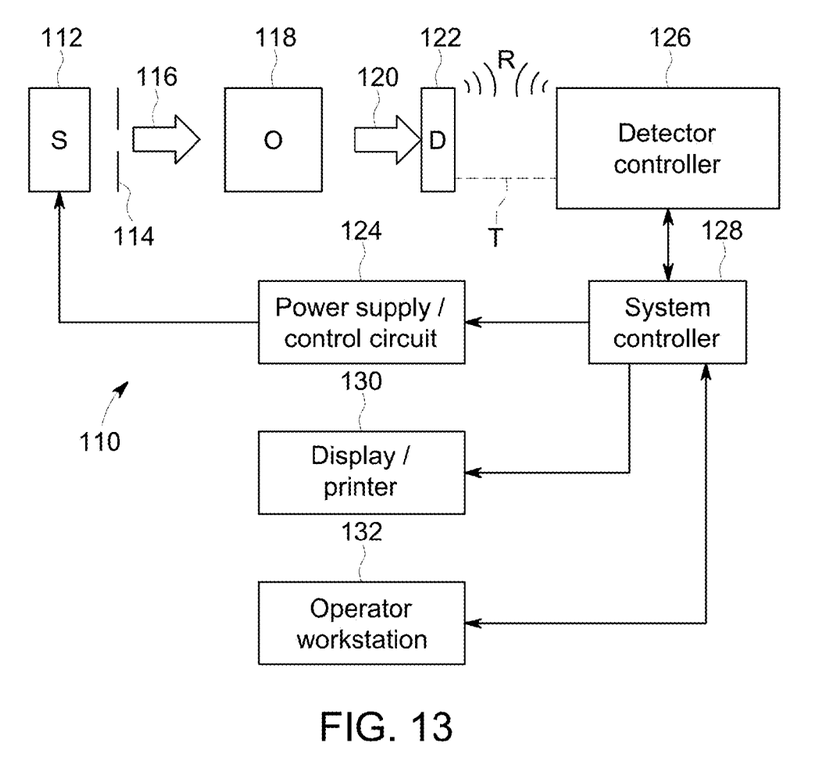
FIG. 13 shows some embodiments of an x-ray imaging system containing a squircle-shaped flat panel detector.

The squircle shaped flat panel detector can be used in any radiographic or fluoroscopic systems. Some embodiments of a radiographic system are depicted in FIG. 13 which illustrates diagrammatically an x-ray system 110 for acquiring and processing image data. In the illustrated embodiment, the x-ray system 110 is a digital X-ray system designed both to acquire original image data and to process the image data for display in accordance with the present technique. In the embodiment illustrated in FIG. 13, x-ray system 110 includes an X-ray radiation source 112 positioned adjacent to a collimator 114. The collimator 114 permits a stream of radiation 116 to pass into a region in which an object or subject 118 is positioned. A portion of the radiation 120 passes through or around the object and impacts a digital X-ray detector, represented generally at reference numeral 122. As will be appreciated by those skilled in the art, the digital X-ray detector 122 may convert the X-ray photons received on its surface to lower energy photons, and subsequently to electric signals, which are acquired and processed to reconstruct an image of the features within the subject.

The X-ray radiation source 112 is controlled by a power supply/control circuit 124 which supplies both power and control signals for examination sequences. Moreover, the digital X-ray detector 122 is communicatively coupled to a detector controller 126 which commands acquisition of the signals generated in the detector 122. In the presently illustrated embodiment, the detector 122 may communicate with the detector controller 126 via any suitable wireless communication standard (R), although the use of digital X-ray detectors 122 that communicate with the detector controller 126 through a cable (T) or some other mechanical connection are also envisaged. The detector controller 126 may also execute various signal processing and filtration functions, such as for initial adjustment of dynamic ranges, interleaving of digital image data, and so forth.

Both the power supply/control circuit 124 and the detector controller 126 are responsive to signals from a system controller 128. In general, the system controller 128 operates the x-ray system 110 to execute examination protocols and to process acquired image data. The system controller 128 can also include signal processing circuitry, typically based upon a programmed general purpose or application-specific digital computer; and associated manufactures, such as optical memory devices, magnetic memory devices, or solid-state memory devices, for storing programs and routines executed by a processor of the computer to carry out various functionalities, as well as for storing configuration parameters and image data; interface circuits; and so forth. In the embodiments illustrated in FIG. 13, the system controller 128 can be linked to at least one output device, such as a display and/or printer 130. The output device may include standard or special purpose computer monitors and associated processing circuitry. One or more operator workstations 132 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The X-ray system 110 as shown in FIG. 13 may also include a variety of alternative embodiments generally configured to meet the particular needs of certain applications. For example, the X-ray system 110 may be either fixed, a mobile system, or a mobile c-arm system where the X-ray detector is either permanently mounted inside one end of the c-arm or removable from the system. Further, the X-ray system 110 may be a table and/or wall stand system in a fixed X-ray room where the X-ray detector 122 is either permanently mounted together with the system or portable. Alternatively, the X-ray system 110 may be a mobile X-ray system with a portable X-ray detector. Such a portable X-ray may be further constructed with a detachable tether or cable used to connect the detector readout electronics to the data acquisition system of the scanner. When not in use, a portable X-ray detector may be detached from the scan station for storage or transfer.

Figure 14:
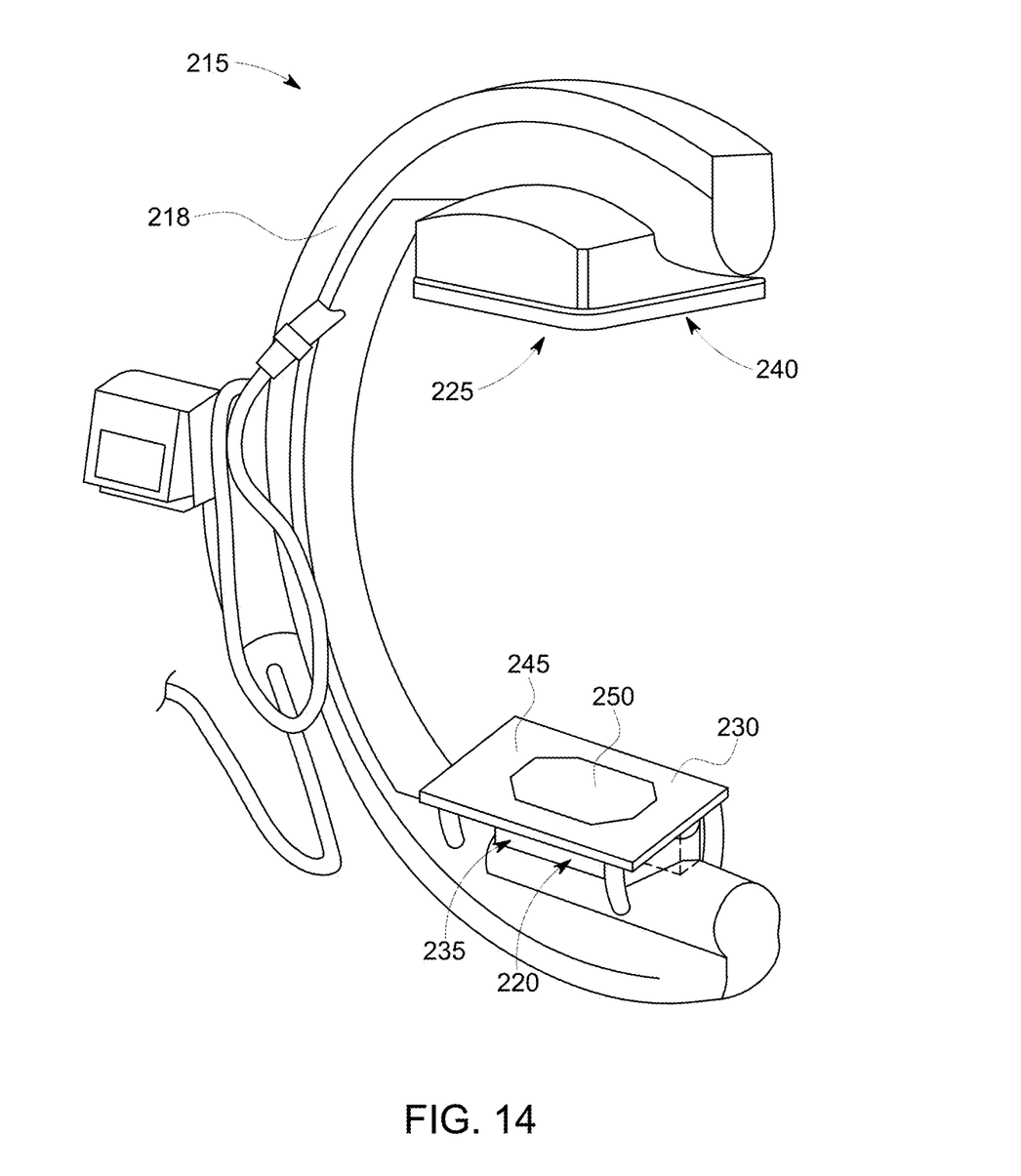
FIG. 14 shows other embodiments of an x-ray imaging system containing a squircle-shaped flat panel detector.

Other embodiments of a radiographic system are depicted in FIG. 14. In these embodiments, the X-ray system can comprise a mobile X-ray device (e.g., an X-ray device comprising a C-arm, a mini C-arm, an O-arm, a non-circular arm, etc.), and a fixed X-ray device. By way of illustration, FIG. 14 shows an X-ray imaging system 215 that comprises a C-arm X-ray device 218 containing the SS flat panel detector.

In the embodiments depicted in FIG. 14, the X-ray system 215 comprises an X-ray source 220, an X-ray detector 225, and a collimator 230. Any suitable X-ray source can be used, including a standard X-ray source, a rotating anode X-ray source, a stationary or fixed anode X-ray source, a solid state X-ray emission source, or a fluoroscopic X-ray source 235 (as shown in FIG. 14). Any suitable X-ray detector can be used, such as an image intensifier or a SS flat panel digital detector 240 (as shown in FIG. 14).

FIG. 14 shows some embodiments in which the collimator 230 comprises an X-ray attenuating material 245 that defines an aperture 250. The collimator 230 can comprise any suitable X-ray attenuating material 245 that allows it to collimate an X-ray beam. Some examples of suitable X-ray attenuating materials include tungsten, lead, gold, copper, tungsten-impregnated substrates (e.g., glass or a polymer impregnated with tungsten), coated substrates (e.g., glass or a polymer coated with tungsten, lead, gold, etc.), steel, aluminum, bronze, brass, rare earth metals, or combinations thereof.

Figure 15:
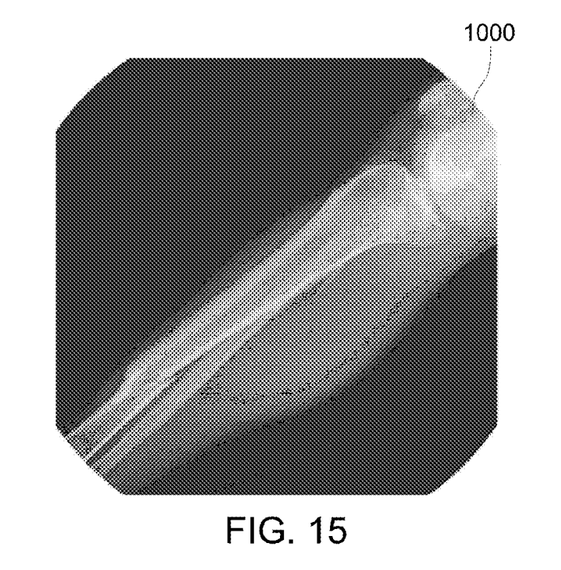
FIG. 15 shows some embodiments of an x-ray image produced by a squircle-shaped flat panel detector.

Using the SS flat panel detector can produce an x-ray image with substantially the same shape as the detector itself. An exemplary x-ray image is illustrated in FIG. 15. In these embodiments, the X-ray image 1000 has a perimeter with a (i) a superellipse shape and (ii) a cornerless shape with at least two substantially straight edges that run substantially perpendicular to each other, wherein such edges do not physically intersect with each other at a 90-degree corner. By having any of the described shapes, the x-ray image can be shown on a relatively large portion of a display area of a display device (e.g., a square or rectangular monitor, screen, projector, TV, etc.), and the entire image can be viewed as it is rotated about its center, without requiring the image to be reshaped or resized. Thus, the x-ray image can maintain its size and geometry during rotation on the display device, while maximizing it's on-screen, image size and the amount of the receptor area of the X-ray detector that is used to take the image.

Using the SS detectors can provide some of the features of a digital flat panel detector (FPD) as well as some of the features of an image intensifier. Both of these devices are typically used as x-ray detectors. The FPD typically have a rectangular or square shape while the image intensifier typically has a circular shape. The FPD often outperforms the x-ray image intensifier in many areas including higher dynamic range, better brightness and spatial resolution uniformity, less veiling glare, no geometric and earth field distortion, etc. But compared to the circular shape of the image intensifier, the corners of the rectangular-shape make the FPD larger in the x-y dimension less ergonomically flexible in imaging systems (i.e., a mobile c-arm). As well, the rectangular corners make it difficult to position a mobile c-arm device in many clinical applications.

In many conventional imaging systems, the image displayed is often rotated an angle for the user to review conveniently. To keep the physical anatomy size from changing during rotation in the FPD, the corners of the images are not used in the imaging process. But this removal makes the corners of the image useless. Indeed, in order to reduce the radiated area on the patient, the collimator of the x-ray source is often designed so that the corners of the detector are not even radiated with x-rays.

With a squircle shape, the active sensing area of the SS detector can be larger than the circular-shaped x-ray image intensifier. In fact, the SS detector can have a sensing area substantially similar to the overlapped area between a square and a circle with the diameter of the circle being between 1× and √2× the square side length.

Figure 16:
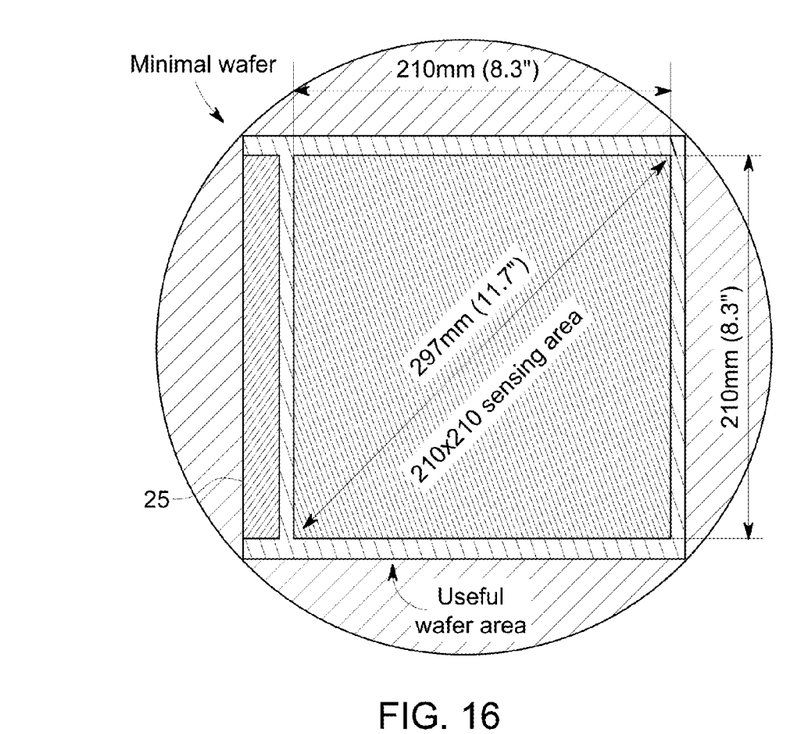
FIG. 16 shows embodiments in which a squircle-shape can save the wafer of a CMOS based flat panel detector.

In addition to the improved ergonomics, using the squircle-shape sensing area utilizes the silicon wafer more efficiently. Industrial standard silicon wafer typically have circular shape with diameters of 1-inch (25 mm), 2-inch (51 mm), 3-inch (76 mm), 4-inch (100 mm), 5-inch (130 mm), 150 mm (5.9"), 200 mm (7.9"), 300 mm (11.8", commonly called 12 inch wafers), and 450 mm (17.7", commonly called 18 inch wafers). But to produce a standard 21 cm square FPD, a single piece of the 12 inch wafer is not big enough, as is seen from FIG. 16. So two combined wafers (or an 18 inch wafer) are used instead to make a 21 cm square FPD. Both of these options cause waste and increase costs. But changing the sensing area to a squircle shape can provide a 21 cm squircle FPD using a 12 inch wafer.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner.

The invention claimed is:

1. A flat panel X-ray detector, comprising:
a circuit board with detector controlling electronics;
a light imager electrically coupled to the circuit board; and
a scintillator coupled to the light imager;
wherein the flat panel X-ray detector has a substantially squircle shape sensing area, wherein the squircle shape is an overlapped area between a square and a circle.

2. The detector of claim 1, wherein the squircle shape has a first substantially straight edge and a second substantially straight edge running substantially perpendicular to the first edge, wherein the first and second edges do not physically intersect with each other at 90 degrees.

3. The detector of claim 2, wherein the squircle shape further comprises a third substantially straight edge and a fourth substantially straight edge running substantially perpendicular to the third edge, and wherein third and fourth edges do not physically intersect with each other at 90 degrees.

4. The detector of claim 3, wherein the first and second edges do not physically intersect with each other at 90 degrees, and wherein the fourth and first edges do not physically intersect with each other at 90 degrees.

5. The detector of claim 3, wherein the squircle shape further comprises a rounded or a curved border between the first and second edges, between the second and third edges, between the third and fourth edges, and between the fourth and first edges.

6. The detector of claim 3, wherein the squircle shape further comprises a chamfered border between the first and second edges, between the second and third edges, between the third and fourth edges, and between the fourth and first edges.

7. The detector of claim 1, further comprising a supporting substrate located between the circuit board and the light imager, wherein the circuit board is located underneath the supporting substrate and electrically coupled to the light imager.

8. An X-ray imaging system, comprising:
an X-ray source; and
a flat panel X-ray detector configured to detect X-rays emanating from the X-ray source, the flat panel X-ray detector including a circuit board with detector controlling electronics; a light imager electrically coupled to the circuit board; and a scintillator coupled to the light imager;
wherein the flat panel X-ray detector has a substantially squircle shape sensing area, and wherein the squircle shape is an overlapped area between a square and a circle.

9. The device of claim 8, wherein the squircle shape has a first substantially straight edge and a second substantially straight edge running substantially perpendicular to the first edge, wherein the first and second edges do not physically intersect with each other at 90 degrees.

10. The device of claim 9, wherein the squircle shape further comprises a third substantially straight edge and a fourth substantially straight edge running substantially perpendicular to the third edge, and wherein third and fourth edges to not physically intersect with each other at 90 degrees.

11. The device of claim 10, wherein the first and second edges do not physically intersect with each other at 90 degrees, and wherein the first and fourth edges do not physically intersect with each other at 90 degrees.

12. The device of claim 10, wherein the squircle shape further comprises a rounded or a curved border between the first and second edges, between the second and second edges, between the third and fourth edges, and between the fourth and first edges.

13. The device of claim 10, wherein the squircle shape further comprises a chamfered border between the first and second edges, between the second and third edges, between the third and fourth edges, and between the fourth and first edges.

14. The device of claim 8, further comprising a supporting substrate located between the circuit board and the light imager, wherein the circuit board is located underneath the supporting substrate and electrically coupled to the light imager.

* * * * *